United States Patent
King, Jr. et al.

(10) Patent No.: US 9,496,626 B2
(45) Date of Patent: Nov. 15, 2016

(54) INSULATION DISPLACEMENT CONNECTOR WITH JOINED BLADE CONNECTORS

(71) Applicants: L. Herbert King, Jr., Chesterfield, MO (US); James Keeven, O'Fallon, MO (US)

(72) Inventors: L. Herbert King, Jr., Chesterfield, MO (US); James Keeven, O'Fallon, MO (US)

(73) Assignee: THE PATENT STORE LLC, O'Fallon, MO (US)

( * ) Notice: Subject to any disclaimer, the term of this patent is extended or adjusted under 35 U.S.C. 154(b) by 0 days.

(21) Appl. No.: 14/756,791

(22) Filed: Oct. 14, 2015

(65) Prior Publication Data

US 2016/0218444 A1     Jul. 28, 2016

Related U.S. Application Data

(60) Provisional application No. 62/125,645, filed on Jan. 27, 2015.

(51) Int. Cl.
*H01R 4/24*       (2006.01)
*H01R 43/16*     (2006.01)
*H01R 13/533*   (2006.01)

(52) U.S. Cl.
CPC .......... *H01R 4/2404* (2013.01); *H01R 13/533* (2013.01); *H01R 43/16* (2013.01)

(58) Field of Classification Search
CPC . H01R 4/2445; H01R 4/2466; H01R 4/2433
USPC ................................. 439/403, 417, 519, 402
See application file for complete search history.

(56) References Cited

U.S. PATENT DOCUMENTS

| 3,521,221 A | 7/1970 | Lmsrts et al. ................... 339/97 |
| 3,636,500 A | 1/1972 | Sedlacek ...................... 339/97 R |
| 3,985,416 A * | 10/1976 | Dola ..................... H01R 4/2433 |
| | | 174/88 R |

(Continued)

OTHER PUBLICATIONS

3M Scotchlok Communication Connectors copyright 2007.

*Primary Examiner* — Gary Paumen
(74) *Attorney, Agent, or Firm* — Jacobson & Johnson LLC

(57) ABSTRACT

A two-gang insulation displacement connector with enhanced electrically connectivity and a method of making the two-gang insulation displacement connector with the insulation displacement connector having a first gang of wire engaging blades having at least two sets of wire engaging blades, which are laterally spaced from each other, and a second gang of wire engaging blades with at least two sets of wire engaging blades with a base of each set of the wire engaging blades in the first gang having a link connecting to a base of each of a set of wire engaging blades in the second gang so that insertion of an insulation covered wire into wire engaging blades of each of gangs forms multiple electrical connections between the wire engaging blades of each gang of the wire engaging blades. In one embodiment the two-gang connector is located in a cover with the open ends of the wire engaging member extending outward for engagement with a housing having a blade guide so that the bringing the cover into engagement with the housing brings the electrical wires into contact with each other while maintaining the gangs in a spaced condition. The cover may include cross protrusions for engagement with cover engagement channels in the housing for locking the cover to the housing. The housing may include axial rails to maintain the cover in axial alignment as the cover and the housing are brought to a closed condition around a set of wires extending into a set of side ports in the housing.

19 Claims, 7 Drawing Sheets

(56) References Cited

U.S. PATENT DOCUMENTS

| | | | |
|---|---|---|---|
| 4,002,391 A | 1/1977 | Dunn et al. | 339/98 |
| 4,295,703 A * | 10/1981 | Osborne | H01R 4/2429 439/403 |
| 4,682,835 A | 7/1987 | Aujla et al. | 439/395 |
| 4,826,449 A | 5/1989 | Debortoli et al. | 439/411 |
| 5,009,612 A * | 4/1991 | Rishworth | H01R 12/616 439/403 |
| 5,120,247 A * | 6/1992 | Audeval | H01R 4/2433 439/403 |
| 6,196,863 B1 * | 3/2001 | Schwant | H01R 12/67 439/417 |
| 7,156,686 B1 * | 1/2007 | Sekela | H01R 12/675 439/403 |
| 7,458,840 B2 | 12/2008 | Pratt | 439/409 |
| 7,789,695 B2 * | 9/2010 | Radle | H01R 4/2433 439/402 |
| 7,934,941 B2 | 5/2011 | Hayauchi | 439/417 |
| 2002/0001996 A1 * | 1/2002 | Seki | H01R 4/2429 439/403 |
| 2006/0199421 A1 * | 9/2006 | Pabst | H01R 12/616 439/403 |

\* cited by examiner

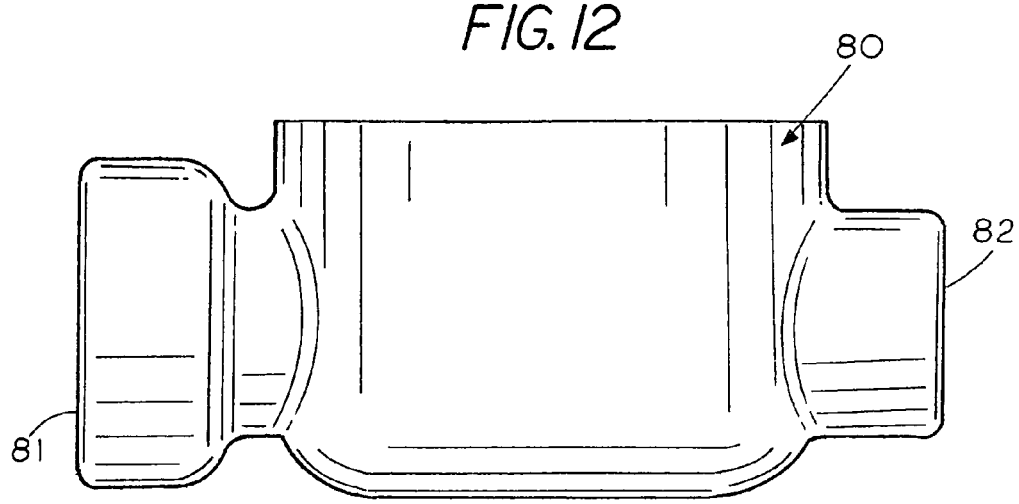
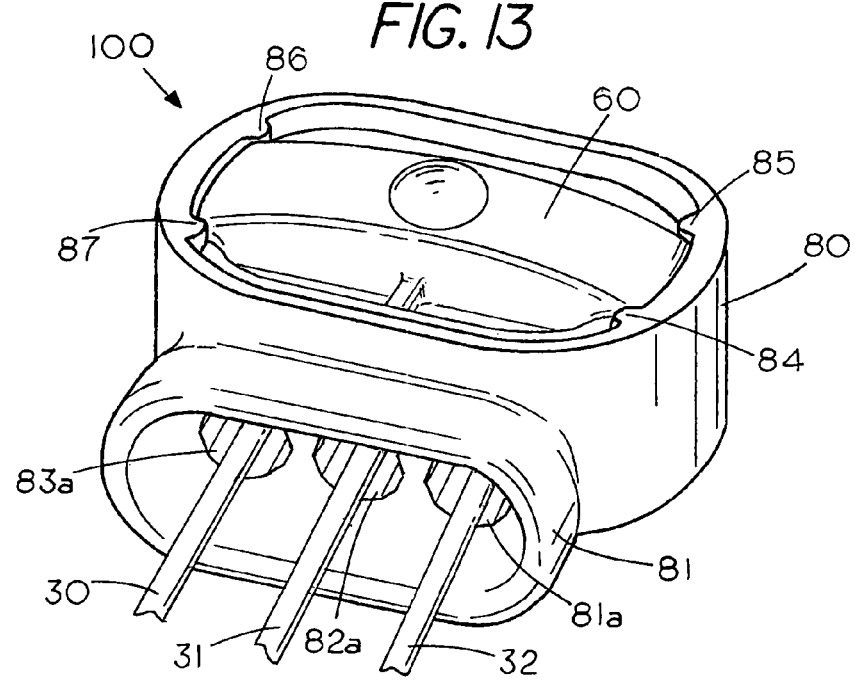

INSULATION DISPLACEMENT CONNECTOR WITH JOINED BLADE CONNECTORS

CROSS REFERENCE TO RELATED APPLICATIONS

This application claims priority from provisional application 62/125,645 filed Jan. 27, 2015.

STATEMENT REGARDING FEDERALLY SPONSORED RESEARCH OR DEVELOPMENT

None

REFERENCE TO A MICROFICHE APPENDIX

None

BACKGROUND OF THE INVENTION

Insulation displacement connectors are well known in the art and typically comprise a pair of cantilevered spaced apart blade members each having an internal edge for penetrating through an outer insulation cover on a wire to bring the edges into electrical contact with the electrical wire. The insulation displacement connectors, which are often referred to as IDC connectors allow one to quickly form an electrical connection between an insulation covered electrical wire and the blade members of the IDC connector without having to manually remove the insulation covering from the wire. The spacing of the blunt edges of the blade from each other are sized so that when an electrical wire with an insulation covering is forced between the blunt edge blades the blunt edged blades penetrate through the soft insulation covering to bring the blunt edge of the blades into electrical contact with the electrical wire. Typically, the spacing between the blades is wider at the top to facilitate insertion of the wire between the blades.

One type of IDC connector, which is shown in U.S. Pat. No. 4,682,835, has the thickness of upper part of the blade at reduced dimensions compared to the lower sections.

U.S. Pat. No. 4,826,449 shows a pair of blades that includes projections on the back edge of the blades to stiffen the blades and increase resistance to outward deformation of the blades during wire insertion at low temperatures.

U.S. Pat. No. 4,002,391 shows an IDC connector with a set of offset swages in the blades to cut the insulation from different sides as the wire is inserted between the blades.

U.S. Pat. No. 3,636,500 shows an IDC connector with that cut a square notch in the insulation through sharp corner edges on the blades that remain in place until engaged by the conducting wire.

U.S. Pat. No. 3,521,221 shows tapered edges on the blade so more than one size electrical wire can be inserted into electrical engagement with the blades.

U.S. Pat. No. 7,934,941 shows an IDC connector, which has a pair of covers that are folded together to clamp the electrical wire therebetween.

U.S. Pat. No. 7,458,840 shows a set of parallel blades that are connected together with different slot spacing between each of the blades. In one pair of blades there is a narrow slot located at the slot entrance of one pair of blades and a wide slot located at the bottom of the blades at the other pair of blades there is a wide slot located at the slot entrance and a narrow slot at the bottom of the slot.

SUMMARY OF THE INVENTION

A two-gang insulation displacement connector with enhanced electrically connectivity and a method of making the two-gang insulation displacement connector with the insulation displacement connector having a first gang of wire engaging blades with at least two sets of wire engaging blades, which are laterally spaced from each other, and a second gang of wire engaging blades with at least two sets of wire engaging blades with a base of each set of the wire engaging blades in the first gang having a link connecting to a base of each of a set of wire engaging blades in the second gang so that insertion of an insulation covered wire into wire engaging blades of each of the gangs forms multiple electrical connections between the wire engaging blades in each gang of the wire engaging blades. In one embodiment the two-gang connector is located in a cover with the open ends of the wire engaging member extending outward for engagement with a housing having a blade guide so that the bringing the cover into engagement with the housing brings the electrical wires into contact with each other while maintaining the gangs in a spaced condition. The cover may include cross protrusions or latches for engagement with cover engagement channels in the housing for holding the cover in a ready condition and for locking the cover to the housing. The housing may include axial rails to maintain the cover in axial alignment as the cover and the housing are brought to a closed condition around a set of wires extending into a set of side ports in the housing.

BRIEF DESCRIPTION OF THE DRAWINGS

FIG. 12 is an end view of the insulation displacement connector housing of FIG. 8; and FIG. 13 is an assembled view of the insulation displacement connector housing and cover.

DESCRIPTION OF THE PREFERRED EMBODIMENT

Figure 1:
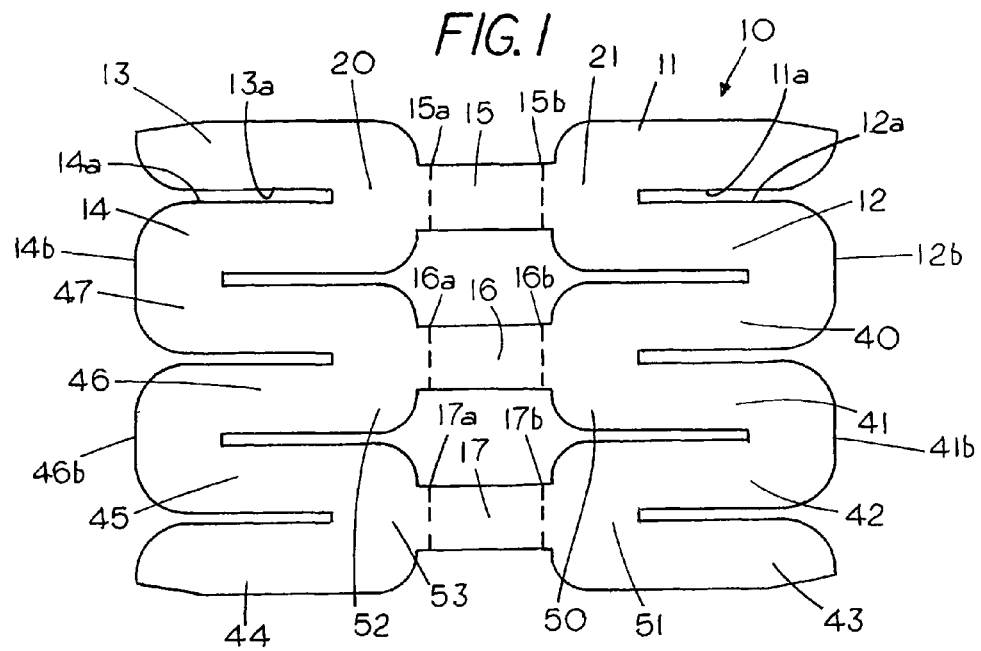
FIG. 1 is a plane view of a compound insulation displacement terminal in an unformed condition.

FIG. 1 is a plane view of a linked two-gang blade connector comprising a one piece insulation displacement terminal 10 in an unformed or planer condition with a first pair of blade connectors 11 and 12 with blade connector 11 having a wire insulation piercing edge 11a and blade connector 12 also having a wire insulation piercing edge 12a with the blade piercing edge 11a and blade piercing edge 12a located in a spaced condition from each other for forming an electrical connection to an insulation covered wire inserted there between. Blade 11 and blade 12 extend from a common base 21.

Insulation displacement terminal 10 includes a second pair of blade connectors 13 and 14 with blade connector 13 having a wire insulation piercing edge 13a and blade 14 also having a wire insulation piercing edge 14a with edge 13a and 14a located in a spaced condition from each other for forming an electrical connection to an insulation covered wire inserted there between. Blade 13 and blade 14 extend from a common base 20.

FIG. 1 shows the one piece compound insulation displacement connector 10 with a first link 15 having a first end 15a seamlessly joined to base 20 and a second end 15b seamlessly joined to base 21 to provide an electrical path between the blades 11, 12 and blades 13, 14. Terminal 10 also includes a second link 16 and a third link 17 with second link 16 having a first end 16a seamlessly joined to base 52, which supports blade connectors 46 and 47 and a second end 16b seamlessly joined to base 50, which supports blade connectors 40 and 41. Similarly, the third link 17 includes a first end 17a seamlessly joined to base 53, which supports blade connectors 44 and 45 and a second end 17b seamlessly joined to base 51, which supports blade connectors 42 and 43. In this example blades 11, 12, 40, 41, 42 and 43 comprise the first gang of blade connectors and connector blades 13, 14, 47, 46, 45 and 44 comprise the second gang of blade connectors with links 15, 16 and 17 electrically connecting each gang of blade connectors to each other.

The one piece compound insulation displacement terminal 10 comprise an electrically conductive material with sufficient rigidity so that the wire engaging edges on the blades can pierce through an insulation covering on an electrical wire as the electrical wire is forced into a slot between adjacent blade connectors, which typically may be made from a resilient electrically conductive metal such as brass.

Figure 2:
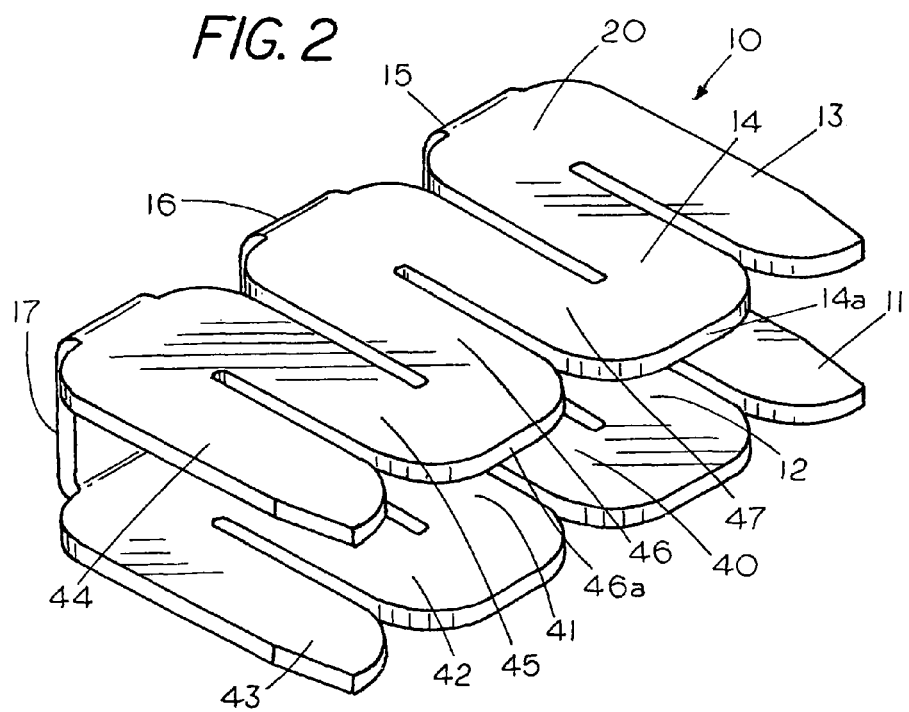
FIG. 2 is perspective view of the compound insulation displacement terminal of FIG. 1 in a formed condition revealing the integral two-gang blade connectors.

FIG. 2 is perspective view of the compound insulation displacement terminal 10 of FIG. 1 in a formed condition revealing that each of the blades 11, 12 and 13, 14 extend at a right angle from link 15. Similarly each of blades 46, 47 and blades 40, 41 extend at a right angle from link 16 and blades 44, 45 and blades 42, 43 extend at a right angle from base 17 with the links maintaining the blades in an upright condition for insertion into a cover of an insulation displacement connector. In the condition the blades 13 and 14 cantileverly extend from one end of base 15 and blades 11 and 12 cantileverly extend from an opposite end of base 15. Similarly, blades 47 and 46 cantileverly extend from one end of base 16 and blades 40 and 41 cantileverly extend from an opposite end of base 16 and blades 45 and 44 cantileverly extend from one end of base 17 and blades 42 and 43 cantileverly extend from an opposite end of base 17.

Figure 3:
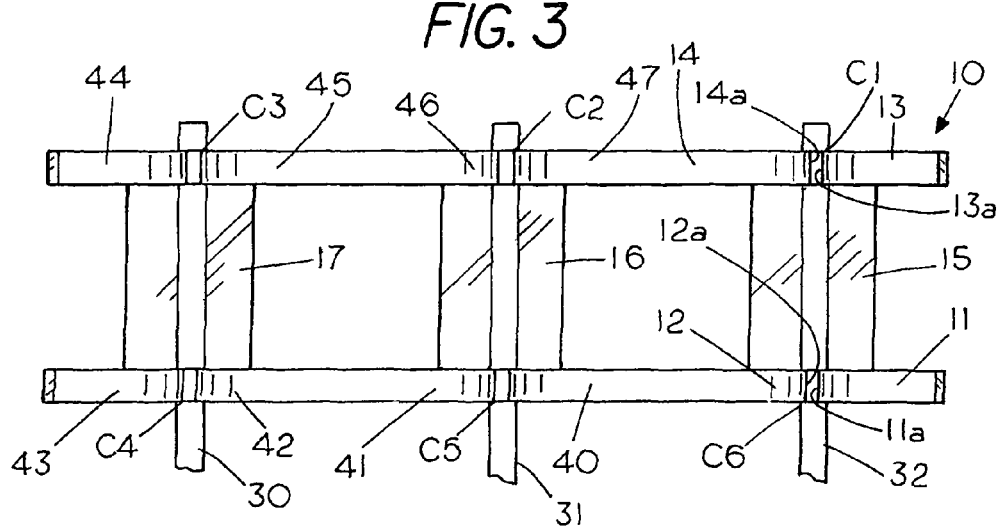
FIG. 3 is a top view of the compound insulation displacement terminal in a formed condition with wires engaged by adjacent connector blades.

FIG. 3 is a top view of the compound insulation displacement terminal 10 in the formed but isolated condition shown in FIG. 2 with each of the blades extending perpendicular to the links there between. As can be seen in FIG. 3 blades 13, 14, 47, 46, 45 and 44 form a first gang connector and blades 11, 12, 40, 41, 42, and 43 form a second gang connector with the blades of each of the gang connectors located in a spaced parallel condition from each other with the slots between each of the blades in one gang are in alignment with the slots in the other gang. A set of links 15, 16 and 17 connecting the bases of each of the blades to each other to provide an electrical path to each of the wires therein as well as forming a compound standalone connector.

FIG. 3 shows the compound insulation displacement terminal 10 with a first wire 32 forming a first electrical connection $C_1$ with blades 13, 14 and a second electrical connection $C_6$ with blades 11, 12. A second electrical wire 31 forms a third electrical connection $C_2$ with blades 46, 47 and a fourth electrical connection $C_5$ with blades 40, 41. Similarly, a third electrical wire 30 forms a fifth electrical connection $C_3$ with blades 44, 45 and a sixth electrical connection $C_4$ with terminal blades 42, 43. In this example the electrical wires with the insulation covering thereon have been forced between adjacent blades enabling the edges on the blades to penetrate the insulation covering and make electrical contact with the electrical wire therein.

In normal operation of the insulation displacement connector 10 the electrical current path from wire 32 to wire 31 extends through connections $C_6$ and $C_5$ and through $C_6$, $C_1$ $C_2$, $C_3$, $C_4$ and $C_5$ and the electrical current path from wire 32 to wire 30 extends through connections $C_6$, $C_1$, $C_2$, $C_3$, and $C_4$ and through $C_6$, $C_5$, and $C_4$.

A feature of the compound one-piece insulation displacement terminal 10 is the additional electrical conduction paths that provide enhanced conduction paths in the event of an open circuit between one of the wires and the blades of the compound insulation displacement connector.

Figure 3A:
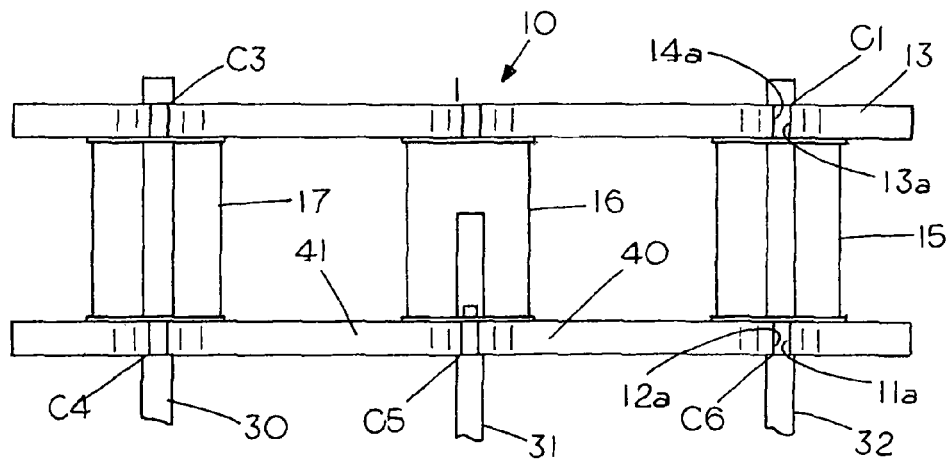
FIG. 3A is a top view of the compound insulation displacement terminal of FIG. 3 in a formed condition with partial wire engagement with the connector blades.

FIG. 3A is an isolated view showing an example of a failed connection that may occur as the insulation blade terminal 10 is forced into electrical contact with a set of electrical wires. More specifically, FIG. 3A shows a top view of the compound insulation displacement connector 10 with a set of identical wires 32, 31, and 30 in electrical engagement therewith. In this example the electrical connection $C_2$ (shown in FIG. 2) is missing as wire 31 forms a single electrical connection $C_5$ with blades 40 and 41. The occurrence of such a single electrical connection is not observable since each of the connections between the blades and the wire is a blind connection. That is, the electrical connections are formed by bringing a cover carrying the blades into engagement with a housing having a wire bed with the cover shielding the blades and wire from view as the blades form the electrical connection within the housing and typically in the presence of a viscous sealant.

In the absences of links 15, 16 and 17 wire 32 would only be connected to wire 31 through connection $C_6$ and $C_5$ and through connections $C_6$, $C_1$, $C_3$, $C_4$ and $C_5$ and wire 31 would be connected to wire 32 through connection $C_5$, $C_4$ and $C_5$, $C_6$, $C_1$ $C_3$ and $C_4$ since there is no $C_2$ connection to wire 31. However, the use of the gang connectors, which are linked to each other, creates multiple electrical paths between wire 31 and wires 30 and 32 through links 15, 16 and 17 thus providing enhanced electrically connective in the event of a failed or improper electrical connection within the wire connector.

Figure 4:
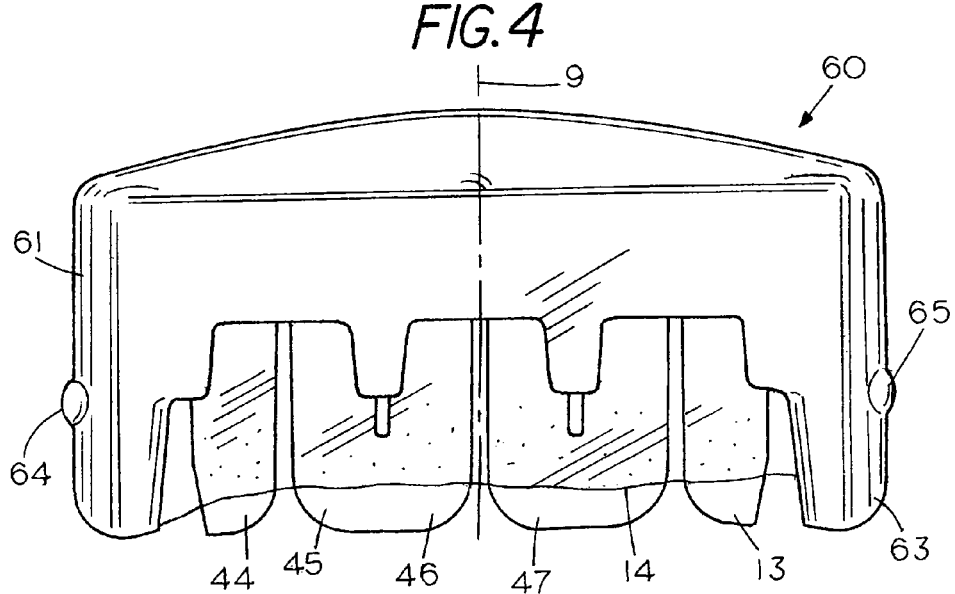
FIG. 4 is a front view of a compound insulation displacement terminal cover with the compound insulation displacement terminal located therein.
Figure 5:
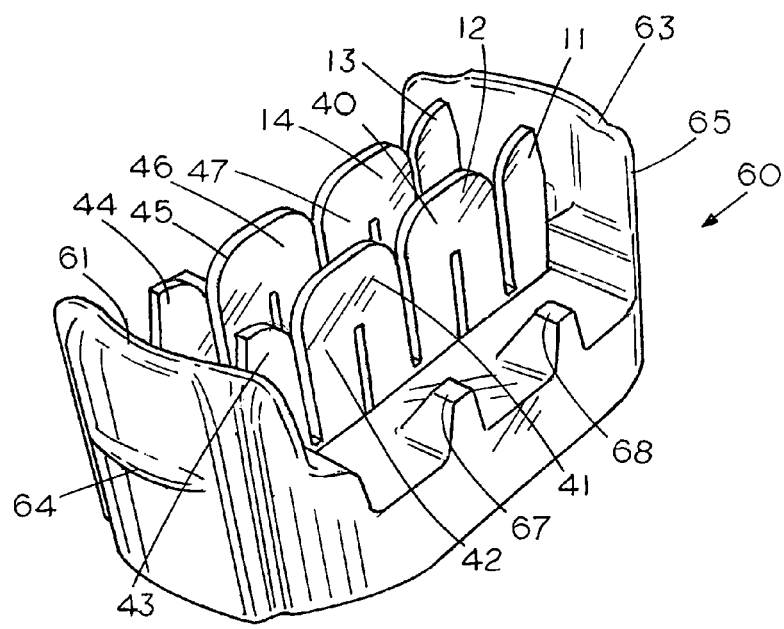
FIG. 5 is a perspective of the compound insulation displacement terminal supported in a cover.

FIG. 4 shows a front view of an insertable cover 60 having a central axis 9 with a viscous insulating gel 69 therein and FIG. 5 shows a perspective view of the insertable cover 60 with the two-gang insulation displacement terminal located therein without the insulation gel 69 therein. In the operational mode the gel 69 is located in the cover and around the blades so that as the blades engage a wire to form electrical contact as the blades are simultaneously covered with a sealant 69 to inhibit corrosion.

FIG. 1, FIG. 2 and FIG. 5 shows six sets of wire engaging blades that provide multiple electrical paths between each other, a first set of wire engaging blades comprising a first blade 13 and a second blade 14, a second set of wire engaging blades comprising blades 46 and 47 a third set of wire engaging blades comprising blades 56 and 44, a fourth set of wire engaging blades comprising blades 11 and 12, a fifth set of wire engaging blades comprising blades 40 and 41 and a sixth set of wire engaging blades comprising blades 42 and 43. In this example a blade top end 14b electrically connects a top end of blade 14 to a top end of an adjacent blade 47, a blade top end 46b electrically connects a top of blade 46 to a top of blade 45, a blade top end 12b connects a top of blade 12 to a top blade 40 and a blade top end 41b electrically connects a top of blade 41 to a top of blade 42, which results in multiple electrical paths between a wire located in engagement with any of the wire engaging blades thus ensuring that if one connection between a wire engaging blade is faulty an alternate path exists to ensure that an electrical connection is formed. This feature becomes useful since the engagement of the wires with the member 10 is not visible since the cover and housing obscure the electrical connection therein.

As can be seen in FIG. 1 and FIG. 2 a first base link 15, a second base link 16 and a third base link 17 supports the six sets of resilient blades in an upright condition. This example shows base links electrically connecting an adjacent blade bases, namely, a base link 15 connects base 20 to base 21, a base link 16 connects base 52 to base 60 and a base link 17 connects base 53 to base 51. As can be seen resilient blades provide a base to base electrical connection and a blade to blade connection between a first electrical wire and a second electrical located in an adjacent resilient blades;

FIG. 4 and FIG. 5 show insertable cover 60 has a general oblong shape with a first end face 61 that protrudes outward for sliding engagement with a mating surface in one end of a housing and a second end face 63 that also protrudes outward for sliding engagement with a mating surface in an opposite end of the housing with the end faces and the mating surfaces enabling the cover to be axially inserted into the housing without the cover binding on the ends of the housing. A transverse latch or protusion 64 is located on end 61 and similarly a transverse latch or protusion 65 is located on the opposite end 63 with both latches located at a common elevation with respect to an axial length. End 63 and 61 enable the latches 64, 65 to hold the cover 60 in either a ready condition or a closed condition where the insulation displacement terminals 10 are in electrical contact with electrical wires in the cover housing.

Figure 6:
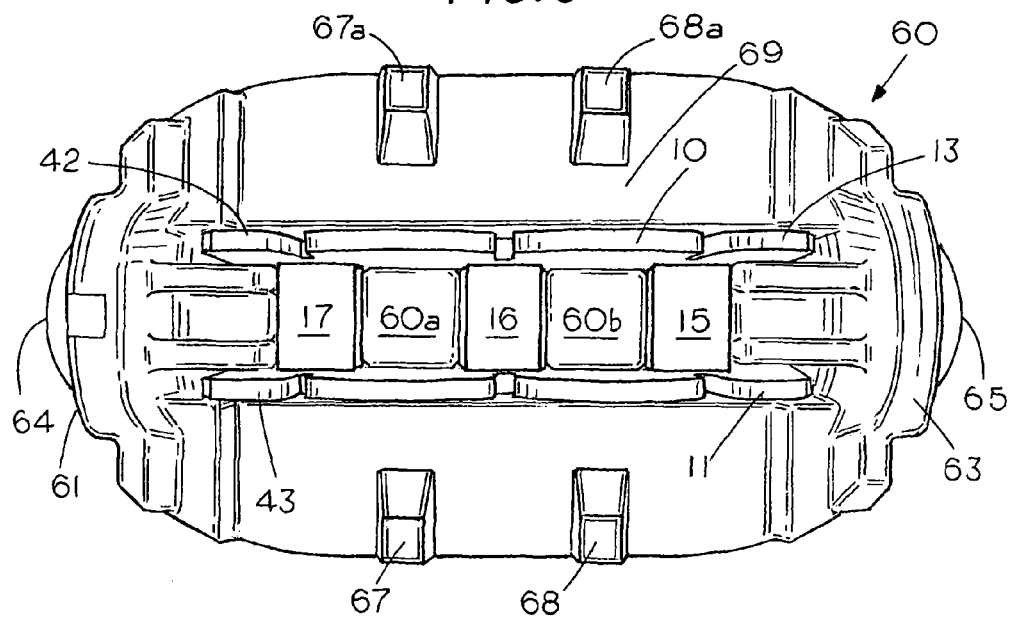
FIG. 6 is a bottom view of a cover with compound insulation displacement terminal located therein.

FIG. 6 shows bottom view of insertable cover 60 without a sealant revealing a set of stops 67, 68 on one side and a similar set of stops 67a, 68a on the opposite side with the insulation displacement terminal 10 centrally located in insertable cover 60. The stops engage similar stops in the housing to limit penetration of the insertable cover 60 into a housing thus insuring that the wires have been sufficiently engaged with the blades therein. The two-gang blade terminals are shown mounted in cover 10 with a links 15, 16 and 17 extending between the blades of each gang. A first four sided locating post 60a extends between links 16 and 17 and a second four sided locating post 60b extends between links 15 and 16 to maintain location of the insulation displacement connector blades 10 in cover 60.

Figure 7:
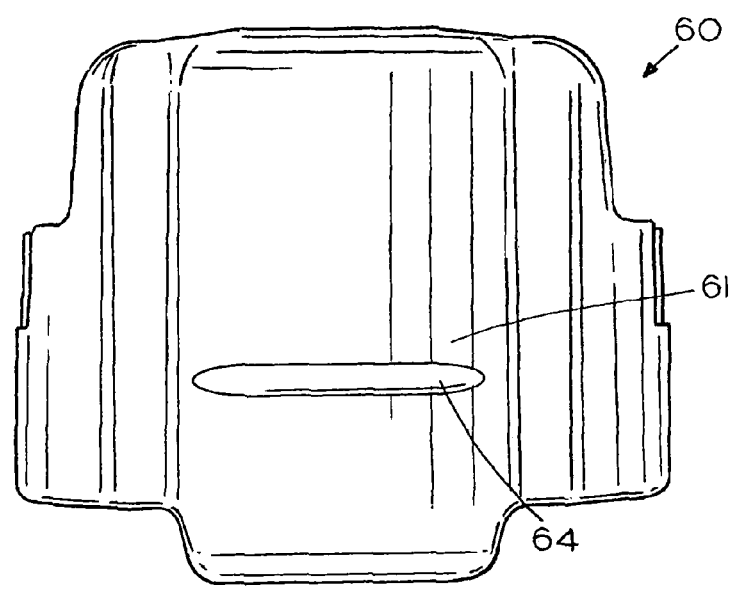
FIG. 7 is an end view of the cover of FIG. 6.

FIG. 7 is an end view of insertable cover 60 revealing the end face 61 for mating sliding engagement with an interior surface on a housing and a transverse latch or protrusion 64 for maintaining the insertable cover 60 in either a ready to use position or in a locked position.

Figure 8:
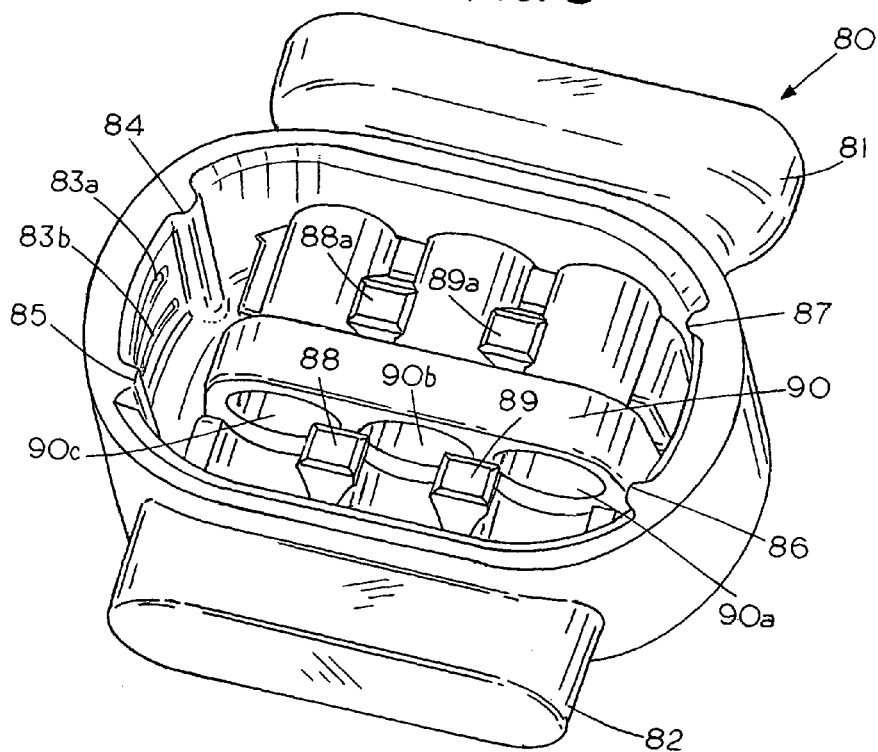
FIG. 8 is a perspective view of an insulation displacement connector housing.
Figure 10:
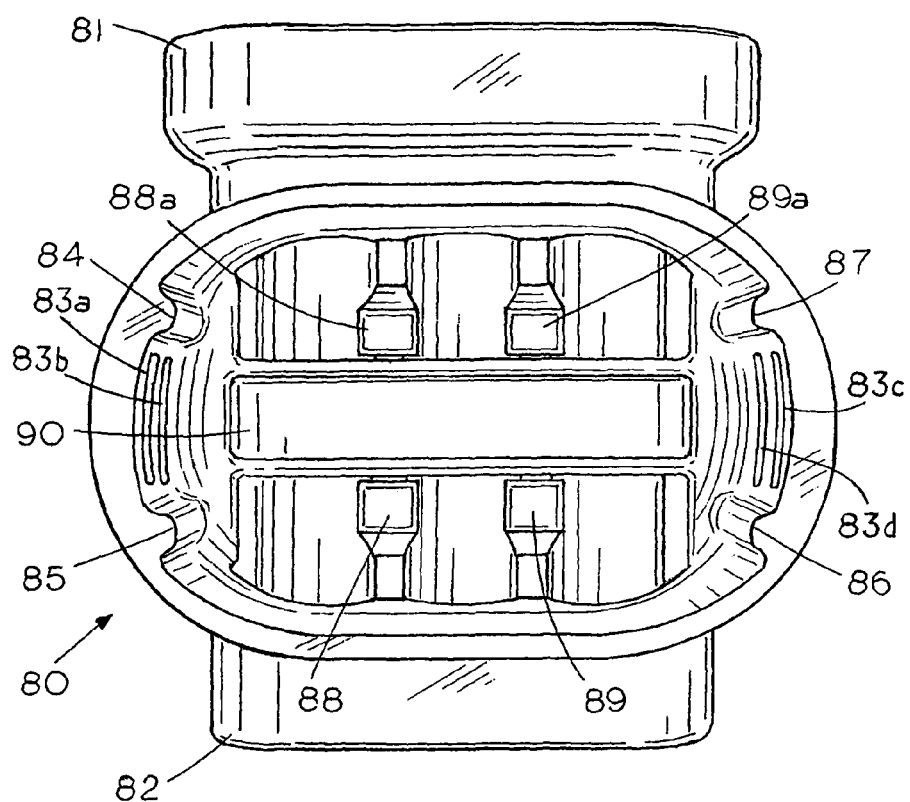
FIG. 10 is a top view of the insulation displacement connector housing of FIG. 8.

FIG. 8 is a perspective view of housing 80 and FIG. 10 is a top view of housing 80. Housing 80 includes a first set of cover stops 88, 89 on one side of a blade guide 90 and a second set of cover stops 88a, 89a located on the opposite side of blade guide 90. Blade guide 90 extends across the housing 90 as shown in FIG. 6. The blade guide 90 has a width slightly less than the spacing between the gangs of blade connectors so the blade guide 90 can be inserted therebetween during the formation of electrical connections in the blades of each of the gang connectors. A set of three wire beds 90a, 90b and 90c are located in blade guide 90 to provide an opening for insertion of an electrical wire therein and support for a wire so that wires therein can be electrically engaged with the two gang of blades in the cover 60 as the cover is brought into locked engagement with the housing 80.

On one end of housing 80 is a top cover storage channel 83a and a lower cover locking channel 83b for engagement with one side of cover 60. Similarly, the other end of housing includes a lower cover locking channel 83d and a top cover storage channel 83c (FIG. 10) with both sets of channels extending crosswise in the neck of the housing to enable the protrusions or latches 64 and 65 on lid 60 to engage the top cover storage side channels in each end of the housing when the connector is in a condition to receive an insulation covered wire and to engage the lower cover locking channels after the wires have been inserted into the wire connector. The cover storage channel holds the cover in place and allows one to insert wires into the housing 80 even though the cover is partially on housing 80a since it keeps the blades from interfering with insertion of the wires into the connector. On the other hand the cover locking channel holds the two gang connector around the wires extending into the housing 80 after the blades have brought into electrical engagement with the electrical wires in the housing 80 through the action of forcing the cover 60 into the housing 80.

Figure 9:
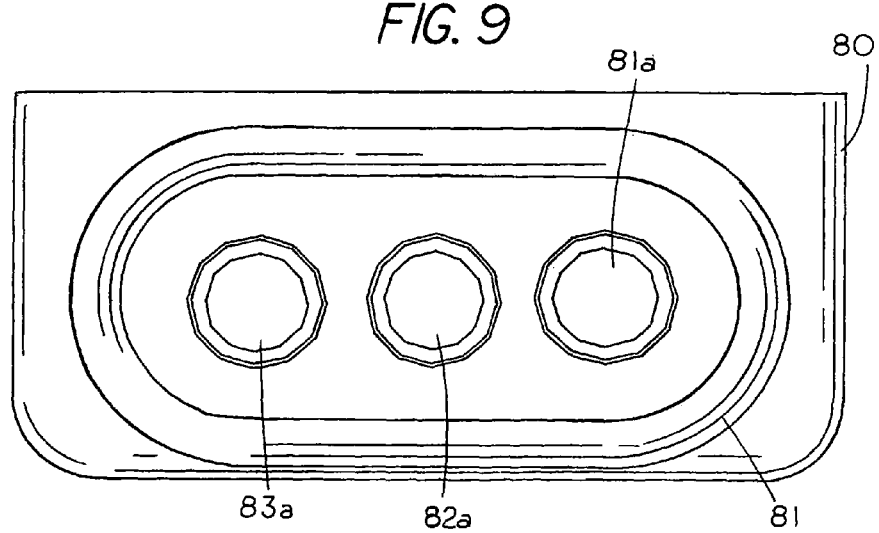
FIG. 9 is a side view of the insulation displacement connector housing of FIG. 8.

FIG. 9 shows an end view of housing 80 revealing the wire ports 81a, 82a and 83a that are located in housing neck 81. In operation wires to be connected to each other are axially inserted into the wire ports 81a, 82a and 83a while the cover 60 is either off the housing 80 or is in a ready condition within a chamber in the housing 80.

FIG. 10 is a top view of the housing 80 revealing the axial rails 84, 85 forming a cover rail guide on one end and the axial rails 86, 87 forming a cover rail guide on the opposite end to maintain the cover 60 in alignment with the housing 80 as the cover is pushed downward into engagement with the housing 80.

Figure 11:
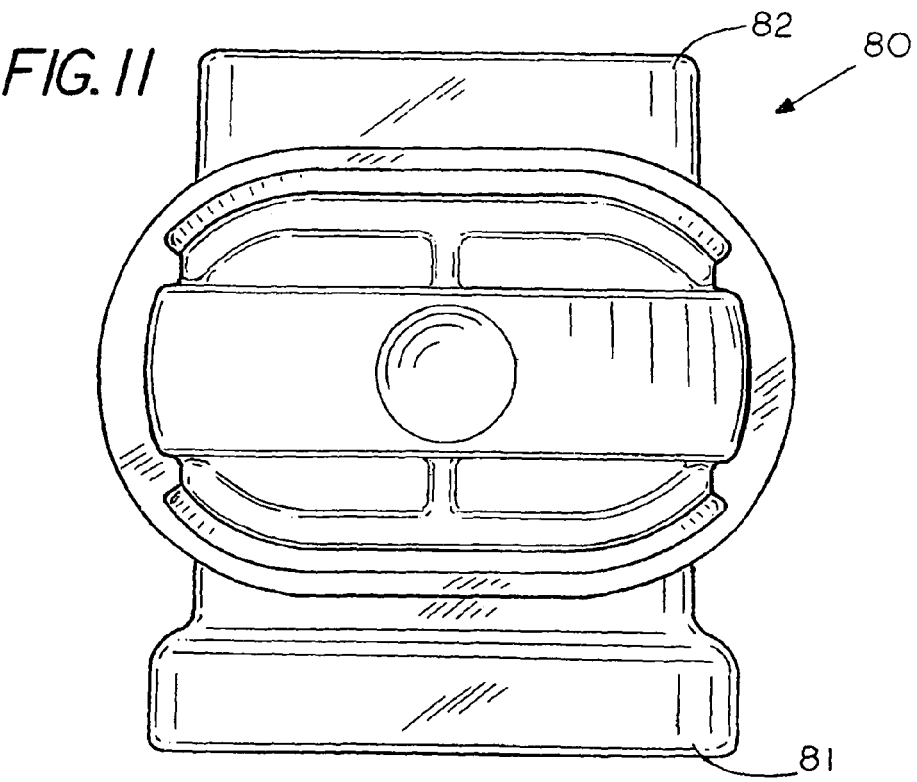
FIG. 11 is a bottom view of the insulation displacement connector housing of FIG. 8.

FIG. 11 is a bottom view of the housing 80 revealing an outward extending neck 81 for insertion of wires therein and a closed extension 82 and FIG. 12 is a side view revealing the wire insertion neck 81 of housing 80 with the closed end 82 located opposite the wire insertion neck 81.

FIG. 13 is an assembled view of the insulation displacement connector 100 showing insertable cover 60 located in a chamber in housing 80 with axial rails 86 and 87 and axial rails 84 and 85 maintaining the cover 60 in axial alignment with housing 80. A wire 30 extends outward from port 83a, a wire 31 extends outward form port 82a and a wire 32 extends outward from wire port 81a with each of the wires electrically connected to each other through a linked two-gang connector 10 which is carried by cover 60 and supported by housing 80 (see FIG. 5). A feature of the invention is bringing a cover 60 with at least four blades in a first gang of wire connector blades and at least four blades in a second gang of wire connector blades into electrical contact with the first wire 30 and the second wire 31 with each of the blades in the first gang of wire connector blades having a base forming an electrical connection to each of the blades in the second gang of wire connector blades to create enhanced conductivity through the existence of multiple electrical paths between the first wire and the second wire even though one of the wire connections between the blades in one of the gang of wire connector blades may be faulty as illustrated in FIG. 3A.

FIG. 13 is a perspective showing the cover 60 in locked engagement with housing 80 with the axial guide rails 86, 85, 87, and 84 coacting to allow for smooth axial insertion of the cover 60 into the housing as the blades in the cover are forced into engagement with the wire 30 in wire port 83*a*, the wire 31 in wire port 82*a* and the wire 32 in wire port 81*a*.

We claim:

1. A low resistance insulation displacement connector comprising;
    a housing having an interior cover storage channel and an interior cover locking channel on each end of the housing with the interior cover storage channel located above the interior cover-locking channel;
    a cover rail guide located in said housing including at least two interior axial rails on each end of the housing with each of the axial rails extending in a transverse direction to the cover locking channel and a cover holding channel;
    a first wire port for axial insertion of a first wire therein;
    a second wire port for axial insertion of a second wire therein;
    a first wire bed for supporting a first wire therein;
    a second wire bed for supporting a second wire therein where the first wire bed and the second wire bed are laterally spaced from each other;
    a one-piece conductor comprising at least four sets of resilient blades each cantileverly extending from a base, each of said set of blades having a first blade with a wire engaging edge laterally spaced from a second blade with a wire engaging edge for stripping insulation from an electrical wire and forming an electrical connection to each of the blades in the set of resilient blades when an electrical wire is forced into a slot between the first blade and the second blade with each of the set of blades having a blade top end electrically connected to a blade top end of an adjacent set of resilient blades and a first base link supporting at least two of the at least four sets of resilient blades in an upright condition and a second base link supporting at least two of the at least four sets of resilient blades in an upright condition with each of the base links electrically connecting a blade base of one of the at least four set of resilient blades to a blade base of another of the at least four set of resilient blades to provide a base to base electrical connection and a blade to blade connection between a first electrical wire and a second electrical located in an adjacent set of resilient blades; and
    a cover carrying the one-piece conductor with the cover containing a viscous sealant, said cover having a first face slideable between the at least two axial rails on one end of the housing and a second end face slideable between the at least two axial rails on the opposite end of the housing as the cover is moved from an open condition where a protrusion on the first end face is in engagement with the cover holding channel on one end of the housing and a protrusion on the second end face is in engagement with the cover holding channel on the opposite end of the housing to a closed condition where the protrusion on the first end face of the housing is in engagement with the cover locking channel on a one end of the housing and the protrusion on the second end face is in engagement with the cover locking channel on the opposite end of the housing.

2. The low resistance insulation displacement connector of claim 1 wherein the one-piece conductor has a U-shape.

3. The low resistance insulation displacement connector of claim 1 wherein each of the blades in the at least four sets of resilient blades extends at a right angle from the base link between two of the at least four sets of resilient blades.

4. The low resistance insulation displacement connector of claim 1 wherein the housing contains a neck for insertion of the cover therein.

5. The low resistance insulation displacement connector of claim 4 wherein the interior cover storage channels and the interior cover locking channels extend crosswise in the neck.

6. The low resistance insulation displacement connector of claim 5 wherein the cover rail guide comprise two rails extending axially along one side of the neck and two rails extending axially along a diametrical opposite side of the neck to maintain the cover in alignment with the housing during the insertion of the cover into the housing.

7. The low resistance insulation displacement connector of claim 6 wherein the interior cover storage channel and the interior cover locking channel on a one end of the neck are located between the two rails extending axially along one side of the neck and the interior cover storage channel and the cover locking channel on the opposite end of the neck are located between the two rails extending axially along the opposite side of the neck with the latch on each end of the cover engageable with the interior cover storage channels in the housing before insertion of a wire therein and engageable with the interior cover locking channels after engagement of the wire with one of the set of blades.

8. An insulation displacement connector with enhanced electrical connectivity comprising:
    a first gang of wire connector blades comprised of at least two sets of electrically conducting wire engaging blades with each set of the wire engaging blades joined to each other and each having a base and a top end and a set of wire insulation piercing edges for removal of insulation from an insulation covered wire inserted therebetween;
    a second gang of wire connector blades spaced laterally from the first gang of wire connector blades with the second gang of wire connector blades joined to each other with the second gang of wire connector blades comprised of at least two sets of electrically conducting wire engaging blades with each set of wire engaging blades in the second gang having a base and a set of wire insulation piercing edges and a top end with the top end of the first set of wire engaging blades electrically joined to the top end of the second gang of wire engaging blades for removal of insulation from an insulation covered wire inserted therebetween;
    a first link extending from a base in the first gang of wire connector blades to the a base in the second gang of wire connector blades to provide a base to base electrical path therebetween; and
    a second link laterally spaced from the first link, said second link extending from a further base in the first gang of wire connector blades to a further base in the second gang to provide a base to base electrical path therebetween.

9. The insulation displacement connector of claim 8 wherein the first link extends at a right angle from the base in the first gang of wire connector blades and at a right angle from the base in the second gang of wire connector blades.

10. The insulation displacement connector of claim 9 including a cover supporting the first gang of wire connector blades and the second gang of wire connector blades in a cantilevered condition.

11. The insulation displacement connector of claim 10 including a housing having a set of wire ports and a blade guide having a width less than a spacing between the first gang of wire connector blades and the second gang of wire connector blades to enable the blade guide to extend between the first gang of wire connector blades and the second gang of wire connector blades when the cover is brought into engagement with the housing.

12. The insulation displacement connector of claim 11 wherein the housing includes a set of axial rails to maintain the cover in alignment with the housing as the cover is pushed into engagement with the housing.

13. The insulation displacement connector of claim 12 wherein the housing and the cover includes a set of crosswise channels and crosswise protrusion for engagement with each other to hold the cover and the housing in a spaced apart condition prior to insertion of a wire into a wire port in the housing and in a locked condition after insertion of the wire into the wire port in the housing.

14. The insulation displacement connector of claim 13 wherein the housing includes a set of internal cover stops to limit axial displacement of the cover into the housing when the first gang of wire connector blades and the second set of wire connector blades are brought into electrical engagement with a wire extending into the housing.

15. A method of forming an electrical connection in an insulation displacement connector having a cover and a housing comprising the steps of:
insertion of a first insulation covered wire into a first wire bed in the housing with the first wire extending into a neck of the housing;
insertion of a second insulation covered wire into a second wire bed in the housing with the second wire extending into a further neck of the housing;
sliding the first end face of a cover between at least two axial rails on a one end of the housing and sliding a second face of a cover between at least two axial rails on the opposite side of the housing;
bringing a protrusion on the first end face of the housing in engagement with a cover locking channel on a one end of the housing and bringing the protrusion on the second end face in engagement with a cover locking channel on the opposite end of the housing thus bringing the at least four blades in a first gang of wire connector blades and at least four blades in a second gang of wire connector blades into electrical contact with the first wire and the second wire where each of the blades in the first gang of wire connector blades have a base forming an electrical connection to each of the blades in the second gang of wire connector blades to form multiple electrical paths between the first wire and the second wire even though one of the wire connections between the blades in one of the gang of wire connector blades may be faulty.

16. The method of claim 15 including the step of displacing the cover from a cover storage channel in the housing by pushing the cover inward into a neck of the housing to force the first insulation covered wire and the second insulation covered wire into electrical communication with each other through a base extending between the first gang of wire connectors and the second gang of wire connectors and continue pushing the cover into the housing until a latch on the cover is brought into engagement with the cover locking channel in the housing.

17. The method of claim 16 including bringing the cover into engagement with the housing until the cover engages a set of internal cover stops in the housing.

18. The method of claim 16 including forming the electrical connection in the presence of a sealant.

19. The method of claim 17 including the step of holding the cover in either a ready condition or a latched condition with a set of transverse latches located on opposite ends of the cover.

* * * * *